United States Patent [19]

Okumura et al.

[11] Patent Number: 4,499,313
[45] Date of Patent: Feb. 12, 1985

[54] PROCESS FOR HYDRATION OF OLEFINS

[75] Inventors: Yoshiharu Okumura, Tokyo; Setsuo Kamiyama; Toshihiro Hosokawa; Katsumi Kaneko, all of Saitama, all of Japan

[73] Assignee: Toa Nenryo Kogyo Kabushiki Kaisha, Tokyo, Japan

[21] Appl. No.: 605,574

[22] Filed: Apr. 30, 1984

[30] Foreign Application Priority Data

May 31, 1983 [JP] Japan .................................. 58-94893

[51] Int. Cl.³ ...................... C07C 29/04; C07C 31/10; C07C 31/12; C07C 31/135
[52] U.S. Cl. ..................................... 568/897; 502/64; 502/71; 502/77; 502/78; 568/715; 568/821; 568/835; 568/838; 568/839
[58] Field of Search ............... 568/897, 839, 838, 835, 568/821, 715

[56] References Cited

U.S. PATENT DOCUMENTS

| 2,663,744 | 12/1953 | Lukasiewicz et al. | 568/897 |
| 3,173,855 | 3/1965 | Misle et al. | 568/897 |
| 3,440,293 | 4/1969 | Rosscup et al. | 568/897 |
| 4,214,107 | 7/1980 | Chang et al. | 568/897 |
| 4,270,011 | 5/1981 | Okumura et al. | 568/899 |
| 4,284,831 | 8/1981 | Okumura et al. | 568/899 |

FOREIGN PATENT DOCUMENTS

| 57-70828 | 5/1982 | Japan . | |
| 124723 | 7/1983 | Japan | 568/897 |
| 1518461 | 5/1976 | United Kingdom . | |

*Primary Examiner*—J. E. Evans
*Attorney, Agent, or Firm*—Rebecca Yablonsky

[57] ABSTRACT

An improved process for producing an alcohol by hydrating an olefin, wherein the improvement comprises hydrating an olefin in the presence of hydrogen-type mordenite or hydrogen-type zeolite Y as a catalyst each having a silica/alumina molar ratio of 20 to 500.

14 Claims, No Drawings

PROCESS FOR HYDRATION OF OLEFINS

FIELD OF THE INVENTION

The present invention relates to a process for hydrating an olefin. More particularly, it relates to a process for hydrating an olefin such as propylene and butene in the presence of a specific solid catalyst, thereby producing the corresponding alcohol.

BACKGROUND OF THE INVENTION

Heretofore, various catalysts have been known for the hydration of olefins, and attempts have been made to use solid catalysts because of their ease of separation and recovery from the reaction product. Usually the hydration of an olefin is favored when the temperature is low and the presence is high. However, such a reaction condition is not practical because the known solid catalysts such as silica, alumina, silica-alumina, mordenite, and zeolite become deactivated by liquid water which is formed in the reaction system.

On the other hand, a hydration process is known which employs a cation exchange resin such as sulfonated styrene-divinylbenzene copolymer as a catalyst. This catalyst exhibits a comparatively high activity for hydration under the condition where there is liquid water. However, it has a drawback. Namely, it irreversibly liberates sulfonic acid groups and becomes greatly deactivated when the reaction temperature is increased, say above 120° C., so as to obtain the industrially desirable reaction rate. The liberated sulfonic acid groups corrode the apparatus. The deactivated catalyst cannot be regenerated by calcination which is commonly employed for inorganic solid catalysts.

Under these circumstances, there has recently been proposed a process for hydrating an olefin by using a specific crystalline aluminosilicate. (U.S. Pat. No. 4,214,107, and Japanese Patent Laid-open No. 70828/1982.) The proposed process, however, is not practical because the catalyst does not have a sufficiently high catalytic activity.

Other patents of interest are U.S. Pat. Nos. 4,270,011 and 4,284,831 and British Pat. No. 1,518,461.

It is an object of this invention to provide a process for hydrating an olefin with a highly active solid catalyst. Applicants have found that this object can be achieved by using as a catalyst hydrogen-type mordenite or hydrogen-type zeolite Y having a specific silica/alumina ratio.

SUMMARY OF INVENTION

The gist of this invention resides in an improved process for producing an alcohol by hydrating an olefin, wherein the improvement comprises hydrating an olefin in the presence of hydrogen-type mordenite or hydrogen-type zeolite Y each having a silica-alumina molar ratio of 20 to 500.

DETAILED DESCRIPTION

Hydration catalyst

The catalyst used in the hydration process of this invention is hydrogen-type mordenite or hydrogen-type zeolite Y each having said specific silica/alumina ratio.

Mordenite occurs naturally and it can also be synthesized. It has a silica/alumina molar ratio of 10 as shown in the following formula:

$$0.5-3.0 M_{2/n}O \cdot Al_2O_3 \cdot 10SiO_2 \cdot 0-50H_2O$$

(wherein M is an alkali metal or alkaline earth metal, and n is a valence of metal M).

The hydration catalyst used in this invention comprises hydrogen-type modernite obtained by treating mordenite so that the silica/alumina molar ratio is raised to 20 to 500. The treatment includes dealkalization, acid extraction, and steam treatment, which are used in combination with one another.

The dealkalization involves replacing a part or all of the alkali metal or alkaline earth metal in mordenite with hydrogen ions. It is this process which produces so called hydrogen-type mordenite. Usually, the dealkalization is accomplished by treating natural mordenite or synthetic mordenite with an aqueous solution of a water-soluble ammonium salt such as ammonium chloride, ammonium nitrate, ammonium sulfate, or ammonium acetate, so that the above-mentioned metal cations in mordenite are replaced by ammonium ions, and then calcining the treated mordenite. The dealkalization is accomplished also by treating natural mordenite or synthetic mordenite with an aqueous solution of an acid such as hydrochloric acid, sulfuric acid, or nitric acid, so that the above mentioned metal cations in mordenite are replaced by hydrogen ions. Dealkalization, however, is not necessarily required, because hydrogen-type mordenite is commercially available and it can be synthesized.

The acid extraction is accomplished by bringing mordenite into contact with a mineral acid such as hydrochloric acid, sulfuric acid, nitric acid, or phosphoric acid, or an organic acid such as acetic acid or formic acid, so that alumina in the mordenite is extracted. The contact with the acid should preferably be carried out at 20° to 120° C. for 1 to 100 hours. The acid extraction may be carried out twice or more. The acid extraction may also serve as the above-mentioned dealkalization. It is desirable that the content of alkali metal or alkaline earth metal in mordenite be reduced to 0.1 wt.% or less (in terms of metal oxide) by the dealkalization and acid extraction.

The steam treatment, which can be combined with the acid extraction, may be carried out by heating mordenite at 150° to 800° C., preferably 300° to 700+ C., for 0.5 to 50 hours, preferably 1 to 30 hours, in the presence of steam.

By using the above described method, it is possible to raise the silica/alumina ratio to 20 to 500. The catalyst having a silica/alumina ratio of 30 to 400 produces a good effect in this invention.

The mordenite used in this invention exhibits the X-ray diffraction pattern as shown in Table 1.

TABLE 1

| Lattice plane space d (Å) | Relative intensity | Lattice plane space d (Å) | Relative intensity |
|---|---|---|---|
| 13.59 ± 0.2 | S | 4.51 ± 0.02 | S |
| 10.16 ± 0.2 | S | 3.97 ± 0.02 | VS |
| 9.15 ± 0.1 | VS | 3.46 ± 0.01 | VS |
| 6.55 ± 0.05 | S | 3.37 ± 0.01 | S |
| 5.80 ± 0.05 | S | 3.22 ± 0.01 | S |

Note:
VS: Very Strong, S: Strong

The other hydration catalyst used in this invention is hydrogen-type zeolite Y having a silica/alumina molar ratio of 20 to 500. It is prepared by removing by extraction alkali metal or alkaline earth metal and aluminum from zeolite Y which is a synthetic zeolite of faujasite type.

The dealkalization and the removal of aluminum are accomplished by bringing zeolite Y into contact with silicon tetrachloride. To be more specific, zeolite Y is dehydrated and dried at 300° to 500° C. and then brought into contact with the vapor of silicon tetrachloride, while being heated from room temperature to 400° to 600° C. This treatment increases the silica/alumina ratio. If it is desirable to increase the silica/alumina ratio further, this treatment may be combined with the above mentioned acid extraction and steam treatment. It is desirable that the content of alkali metal or alkaline earth metal in zeolite Y be 0.1 wt% or less, and the silica/alumina ratio be 30 to 400.

The hydrogen-type zeolite Y used in this invention exhibits the X-ray diffraction pattern as shown in Table 2.

TABLE 2

| Lattice plane space d (Å) | Relative intensity | Lattice plane space d (Å) | Relative intensity |
|---|---|---|---|
| 14.71 ± 0.2 | VS | 3.410 ± 0.07 | W |
| 8.83 ± 0.2 | S | 3.276 ± 0.07 | S |
| 7.43 ± 0.2 | S | 2.976 ± 0.07 | W |
| 5.71 ± 0.1 | S | 2.873 ± 0.07 | M |
| 4.71 ± 0.1 | M | 2.820 ± 0.07 | S |
| 4.33 ± 0.1 | S | 2.720 ± 0.05 | W |
| 3.86 ± 0.1 | W | 2.655 ± 0.05 | W |
| 3.734 ± 0.07 | S | 2.597 ± 0.05 | M |

Note:
M: Medium, W: Weak

OLEFIN

The olefin that can be hydrated according to the process of this invention includes linear, branched, and cyclic olefins. It also includes terminal olefins and internal olefins. Suitable olefins are monoolefins of carbon number 2 to 12, preferably 2 to 8. Examples of such monoolefins include ethylene, propylene, 1-butene, 2-butene, isobutene, pentenes, hexenes, heptenes, octenes, cyclobutene, cyclopentene, cyclohexene, methylcyclopentene, methylcyclohexene, cyclooctene, and styrene. The process of this invention can favorably be applied to the hydration of linear alpha or internal monoolefins and cyclic monoolefins of carbon number 2 to 6 such as ethylene, propylene, 1-butene, 2-butene, pentenes, hexenes, and cyclohexene. The above-mentioned olefins may be used in combination with one another or with a non-olefin compound such as an alkane.

PROCESS OF HYDRATION

The present invention is intended to react an olefin with water in the presence of a hydration catalyst, thereby producing a corresponding alcohol. The hydration reaction is carried out batchwise or continuously by using a fixed bed or fluidized bed containing the hydration catalyst.

One mole of olefin is brought into contact with 1 to 20 mol of water. The reaction temperature is usually 50° to 300° C., and preferably 100° to 250° C. The reaction pressure is 5 to 200 kg/cm² which is high enough to maintain the liquid phase or gas-liquid multi-phase in the reaction system. The reaction time is usually 20 minutes to 20 hours in the case of batchwise reaction, and the LHSV is usually 0.1 to 10 in the case of continuous reaction.

It is by this hydration reaction that an olefin is hydrated and converted to the corresponding alcohol. This invention is particularly useful for producing isopropanol from propylene and sec-butanol from 1-butene or 2-butene.

The process of this invention makes it possible to produce alcohol in higher yields than the hydration process that employs a conventional inorganic solid acid. Unlike the hydration process that employs an ion-exchange resin as a catalyst, the process of this invention is not restricted by the hydration temperature and is free of problems caused by the separation of the acid components. The hydration catalyst used in this invention can be regenerated by calcination which is commonly employed for inorganic solid catalysts.

The invention is now described in more detail with reference to the following examples, in which "%" is based on weight, unless otherwise noted.

EXAMPLES 1 TO 8 AND COMPARATIVE EXAMPLES 1 TO 3

Preparation of hydration catalysts

Synthetic mordenite (Zeolon 900Na, a product of Norton Co.) was treated with a 10% aqueous solution of ammonium chloride (15 cc for 1 g of mordenite) at 80° C. for 1.5 hours, and then the aqueous solution was removed. This step was repeated three times. The mordenite was thoroughly washed and dried at 120° C. and finally calcined at 600° C. for 3 hours. Thus there was obtained hydrogen-type mordenite containing 0.1% of $Na_2O$ and having a silica/alumina molar ratio (referred to as S/A hereinafter) of 10. This mordenite is designated as catalyst A.

Catalyst A was treated with 12N hydrochloric acid (15 cc for 1 g of catalyst A) at 90° C. for 8 hours. The treated catalyst A was washed with water until chlorine ion was not detected any longer, and then dried at 120° C. and finally calcined at 600° C. for 3 hours in air. Thus there was obtained hydrogen-type mordenite containing 0.07% of $Na_2O$ and having an S/A of 18. This mordenite is designated as catalyst B.

Catalyst B was treated with 12N hydrochloric acid (15 cc for 1 g of catalyst B) at 90° C. for 20 hours. The treated catalyst B was washed with water until chlorine ion was not detected any longer, and then dried at 120° C. and finally calcined at 600° C. for 3 hours in air. Thus, there was obtained hydrogen-type mordenite containing 0.03% of $Na_2O$ and having an S/A of 32. This mordenite is designated as catalyst C.

Catalyst B was treated twice with hydrochloric acid at 90° C. for 20 hours, washed with water, dried, and calcined in the same way as above. Thus there was obtained catalyst D containing 0.02% of $Na_2O$ and having an S/A of 55.

Catalyst D was treated with hot air containing 10% of steam at 700° C. for 3 hours and then treated with 12 N hydrochloric acid at 90° C. for 4 hours. The treated catalyst D was washed with water, dried, and calcined in the same way as above. Thus there was obtained catalyst E containing 0.015% of $Na_2O$ and having an S/A of 77.

Catalyst E was treated twice with hydrochloric acid at 90° C. for 20 hours, and then washed with water, dried, and calcined in the same way as above. Thus there was obtained catalyst F containing 0.01% of $Na_2O$ and having an S/A of 114.

Catalyst F was repeatedly subjected to steam treatment and acid extraction in the same way as above in order to increase the silica/alumina ratio. Thus there were obtained catalysts G to K containing $Na_2O$ and having S/A as follows:

Catalyst G ($Na_2O$:0.007%, S/A: 149)
Catalyst H ($Na_2O$:0.005%, S/A: 197)
Catalyst I ($Na_2O$:0.004%, S/A: 293)
Catalyst J ($Na_2O$:0.003%, S/A: 410)
Catalyst K ($Na_2O$:0.002%, S/A: 588)

The hydration catalyst A to K prepared as above gave the same X-ray diffraction pattern as shown in Table 1. This indicates that the crystal structure of mordenite was not affected by the treatment.

Hydration reaction of olefin 15 ml of hydration catalysts A to K was introduced into a stainless steel reactor tube. A mixture of water and 1-butene (10:1 in mol) was fed continuously to the reactor tube at an LHSV of 1.5 $hr^{-1}$, and the hydration reaction was carried out at 140° C. and under 45 $kg/cm^2G$. The results are shown in Table 3. It is noted that sec-butanol which is the desired product, is obtained in high yields with the catalysts having the specific range of silica/alumina ratio. The formation of by-products such as sec-butyl ether and octene was very small in all the cases.

TABLE 3

| Example No. | Hydration catalyst | Silica/alumina (molar ratio) | Yield of SBA (mol %) | Space time yield of SBA (g/l/hr) |
|---|---|---|---|---|
| Comparative Example 1 | A | 10 | 0 | 0 |
| Comparative Example 2 | B | 18 | 0.3 | 1.2 |
| Example 1 | C | 32 | 1.0 | 4.0 |
| Example 2 | D | 55 | 2.9 | 12 |
| Example 3 | E | 77 | 9.0 | 36 |
| Example 4 | F | 114 | 11.5 | 46 |
| Example 5 | G | 149 | 8.3 | 33 |
| Example 6 | H | 197 | 7.0 | 28 |
| Example 7 | I | 293 | 3.8 | 15 |
| Example 8 | J | 410 | 2.8 | 11 |
| Comparative Example 3 | K | 588 | 0.4 | 1.6 |

Note:
SBA: Sec-butanol

COMPARATIVE EXAMPLE 4

Zeolite Y ("SK-40", a product of Linde in U.S., $Na_2O$:7.7%, S/A:4) was subjected to dealkalization treatment, followed by washing, drying, and calcination, the same way as in the preparation of catalyst A in Example 1, by using 15 cc of a 10% aqueous solution of ammonium chloride for 1 g of zeolite. Thus there was obtained hydrogen-type zeolite Y containing 0.2% of $Na_2O$ and having an S/A of 4. Using this zeolite Y as the hydration catalyst, the hydration of 1-butene was carried out in the same way as in Example 1. The yield of sec-butanol was less than 0.1 mol%.

COMPARATIVE EXAMPLE 5

The hydration of 1-butene was carried out in the same way as in Example 1, by using silica-alumina ("N632"-HN", a product of Nikki Co., silica 75% and alumina 25%) as a hydration catalyst. The yield of sec-butanol was less than 0.2 mol%.

COMPARATIVE EXAMPLE 6

The hydration of 1-butene was carried out in the same way as in Example 1, by using molecular sieve 10X (calcium X, a product of Union Showa Co.) as a hydration catalyst. The yield of sec-butanol was less than 0.1 mol%.

COMPARATIVE EXAMPLE 7

Preparation of hydration catalyst

Crystalline aluminosilicate (ZSM-5) was prepared as follows according to the method described in U.S. Pat. No. 3,965,207. 7.4 parts of aluminum sulfate was dissolved in 195 parts of pure water. To the solution were added 26.5 parts of sulfuric acid, 17.8 parts of tetrapropylammonium bromide, and 86 parts of sodium chloride. Thus there was obtained an aluminum sulfate solution. This aluminum sulfate solution was added with stirring to a mixture of 142 parts of water and 281 parts of water glass ($Na_2O$:9.5%, $SiO_2$:28.6%). The resulting mixture was transferred to a stainless steel autoclave and heated therein with stirring at 160° C. for 20 hours. The crystallized solid product was dried at 110° C. and then calcined at 600° C. for 3 hours. The resulting solid was found to have the crystal structure of ZSM-5 by X-ray analysis.

This ZSM-5 was treated with 1N ammonium chloride aqueous solution at 90° C. for 10 hours, followed by drying at 110° C. and calcination at 600° C. for 3 hours in air. Thus there was obtained hydrogen-type ZSM-5 (HZSM-5) containing 0.01% of $Na_2O$ and having an S/A of 111.

Hydration of olefin

Using the HZSM-5 as a hydration catalyst, the hydration of 1-butene was carried out in the same way as in Example 1. The yield of sec-butanol was 0.3 mol%.

EXAMPLES 9 TO 13 AND COMPARATIVE EXAMPLE 8

Preparation of hydration catalyst

The Zeolite Y as used in Comparative Example 4 was placed in a quartz tube and was dried in a dry nitrogen stream at 380° C. for 2 hours. After cooling to room temperature, nitrogen saturated (at room temperature) with silicon tetrachloride was fed to the quartz tube at a rate of 300 ml/min for 10 g of zeolite Y. During feeding, the quartz tube was heated at a rate of 4° C./min from room temperature. After the temperature had reached 500° C., the feeding of nitrogen saturated with silicon tetrachloride was continued for 1 hour. The zeolite Y was cooled by feeding nitrogen to the quartz tube, washed with water until chlorine ion was not detected any longer and finally dried at 200° C. for 8 hours. Thus there was obtained hydrogen-type zeolite Y (catalyst L) containing 0.05% of $Na_2O$ and having an S/A of 30.

Hydrogen-type zeolite Y (catalyst M) containing 0.04% of $Na_2O$ and having an S/A of 45 was prepared in the same way as for catalyst L, except that the treatment with silicon tetrachloride at 500° C. was extended to 1.5 hours.

Hydrogen-type zeolite Y (catalyst N) containing 0.02% of $Na_2O$ and having an S/A of 99 was prepared in the same way as for catalyst L, except that the treatment with silicon tetrachloride at 500° C. was extended to 2.5 hours.

Catalyst M was treated with 2N hydrochloric acid (20 cc for 1 g of catalyst M) at 80° C. for 8 hours. The treated catalyst M was washed with water until chlorine ion was not detected any longer and dried at 120° C. Thus there was obtained hydrogen-type zeolite Y (catalyst O) containing 0.01% of $Na_2O$ and having an S/A of 204.

Catalyst O was treated with hydrochloric acid three times and washed and dried in the same way as above. Thus there was obtained hydrogen type zeolite Y (catalyst P) containing 0.006% of $Na_2O$ and having an S/A of 457.

Catalyst P was treated with 2N hydrochloric acid (20 cc for 1 g of catalyst P) at 80° C. for 8 hours. The treated catalyst P was washed with water until chlorine ion was not detected any longer and dried at 120° C. Thus there was obtained hydrogen-type zeolite Y (catalyst Q) containing 0.005% of $Na_2O$ and having an S/A of 550.

The catalysts L to Q thus obtained exhibited X-ray diffraction patterns as shown in Table 2. This indicates that they maintain the crystal structure of zeolite Y.

Hydration reaction of olefin

The hydration reaction of 1-butene was carried out in the same way as in Example 1, by using the above catalysts as the hydration catalysts. The results are shown in Table 4.

TABLE 4

| Example No. | Hydration catalyst | Silica/alumina (molar ratio) | Yield of SBA (mol %) | Space time yield of SBA (g/l/hr) |
| --- | --- | --- | --- | --- |
| Example 9 | L | 30 | 1.2 | 4.8 |
| Example 10 | M | 45 | 2.6 | 10 |
| Example 11 | N | 99 | 10.3 | 41 |
| Example 12 | O | 204 | 6.8 | 27 |
| Example 13 | P | 457 | 2.7 | 11 |
| Comparative Example 8 | Q | 550 | 0.9 | 3.6 |

EXAMPLES 14 TO 19

The hydration reaction of olefins other than 1-butene was carried out under different conditions. The results are shown in Table 5.

TABLE 5

| Example | Olefin | Hydration catalyst | Olefin/water (molar ratio) | LHSV (hr$^{-1}$) | Temperature (°C.) | Pressure (kg/cm$^2$) | Alcohol formed | Yield of alcohol (mol %) |
| --- | --- | --- | --- | --- | --- | --- | --- | --- |
| 14 | Ethylene | D | 15 | 4 | 210 | 150 | Ethanol | 6.8 |
| 15 | Propylene | L | 12 | 2 | 160 | 100 | Isopropanol | 18 |
| 16 | 2-Butene | E | 10 | 1.5 | 140 | 80 | Sec-butanol | 10 |
| 17 | 1-Pentene | F | 8 | 1 | 135 | 60 | 2-Pentanol | 6.5 |
| 18 | 1-Hexene | G | 6 | 0.8 | 140 | 50 | 2-Hexanol | 5.6 |
| 19 | Cyclohexene | M | 6 | 0.7 | 130 | 40 | Cyclohexanol | 5.1 |

What is claimed is:

1. An improved process for producing an alcohol by hydrating an olefin, wherein the improvement comprises hydrating an olefin in the presence of hydrogen-type mordenite or hydrogen-type zeolite Y as a catalyst each having a silica/alumina molar ratio of 20 to 500.

2. The process according to claim 1 in which the catalyst has a silica/alumina molar ratio in the range of 30 to 400.

3. The process according to claim 1 in which said hydrogen-type mordenite is obtained by dealkalization, acid extraction and steam treatment of mordenite.

4. The process according to claim 1 in which said hydrogen-type mordenite is obtained by acid extraction and steam treatment.

5. The process according to claim 1 in which said hydrogen-type mordenite exhibits the following X-ray diffraction pattern:

| Lattice plane space d (Å) | Relative intensity | Lattice plane space d (Å) | Relative intensity |
| --- | --- | --- | --- |
| 13.59 ± 0.2 | S | 4.51 ± 0.02 | S |
| 10.16 ± 0.2 | S | 3.97 ± 0.02 | VS |
| 9.15 ± 0.1 | VS | 3.46 ± 0.01 | VS |
| 6.55 ± 0.05 | S | 3.37 ± 0.01 | S |
| 5.80 ± 0.05 | S | 3.22 ± 0.01 | S |

6. The process according to claim 1 in which said hydrogen type zeolite Y is obtained by removing by extraction alkali metal or alkaline earth metal and aluminum from zeolite Y.

7. The process according to claim 6 in which the dealkalization and removal of aluminum are accomplished by bringing zeolite Y into contact with silicon tetrachloride.

8. The process according to claim 7 in which said hydrogen-type zeolite Y has a content of alkali metal or alkaline earth metal of 0.1 wt.% or less and the silica-alumina molar ratio is in the range of 30 to 400.

9. The process according to claim 1 in which said hydrogen-type zeolite Y exhibits the following X-ray diffraction pattern:

| Lattice plane space d (Å) | Relative intensity | Lattice plane space d (Å) | Relative intensity |
| --- | --- | --- | --- |
| 14.71 ± 0.2 | VS | 3.410 ± 0.07 | W |
| 8.83 ± 0.2 | S | 3.276 ± 0.07 | S |
| 7.43 ± 0.2 | S | 2.976 ± 0.07 | W |
| 5.71 ± 0.1 | S | 2.873 ± 0.07 | M |
| 4.71 ± 0.1 | M | 2.820 ± 0.07 | S |
| 4.33 ± 0.1 | S | 2.720 ± 0.05 | W |
| 3.86 ± 0.1 | W | 2.655 ± 0.05 | W |
| 3.734 ± 0.07 | S | 2.597 ± 0.05 | M |

10. The process according to claim 1 in which the olefin has from 2 to 12 carbon atoms.

11. The process according to claim 10 in which the olefin has from 2 to 8 carbon atoms.

12. The process according to claim 11 in which the olefin is aliphatic having from 2 to 6 carbon atoms, or is cyclohexene.

13. The process according to claim 1 in which isopropanol is produced from propylene or secbutanol is produced from 1-butene or 2-butene.

14. The process according to claim 12 in which the reaction temperature is in the range of 130° C. to 210° C.

* * * * *